US009539399B2

(12) United States Patent
Abu.Talib et al.

(10) Patent No.: US 9,539,399 B2
(45) Date of Patent: Jan. 10, 2017

(54) SAFETY SYRINGE

(75) Inventors: Abd.Rahim Abu.Talib, Selangor (MY); Adi Azriff Basri, Selangor (MY); Siti Zuraifah Mohd.Zabidi, Selangor (MY); Mohd Salleh Yahaya, Selangor (MY); Khairi Mat.Isa, Selangor (MY)

(73) Assignees: UNIVERSITI PUTRA MALAYSIA, Selangor (MY); SELIA-TEK MEDICAL SDN.BHD, Selangor (MY)

( * ) Notice: Subject to any disclaimer, the term of this patent is extended or adjusted under 35 U.S.C. 154(b) by 0 days.

(21) Appl. No.: 14/130,988

(22) PCT Filed: Jul. 11, 2012

(86) PCT No.: PCT/MY2012/000202
§ 371 (c)(1),
(2), (4) Date: Feb. 21, 2014

(87) PCT Pub. No.: WO2013/009166
PCT Pub. Date: Jan. 17, 2013

(65) Prior Publication Data
US 2014/0171866 A1    Jun. 19, 2014

(30) Foreign Application Priority Data

Jul. 14, 2011  (MY) .......................... PI2011700110

(51) Int. Cl.
*A61M 5/50* (2006.01)
*A61M 5/32* (2006.01)
*A61M 5/315* (2006.01)

(52) U.S. Cl.
CPC ............ *A61M 5/50* (2013.01); *A61M 5/3205* (2013.01); *A61M 5/31511* (2013.01); *A61M 5/31515* (2013.01); *A61M 2005/3279* (2013.01)

(58) Field of Classification Search
CPC .. A61M 5/50; A61M 5/3205; A61M 5/31511; A61M 5/31515; A61M 2005/3279
(Continued)

(56) References Cited

U.S. PATENT DOCUMENTS 3,320,954 A * 5/1967 Cowley .................. A61M 5/34
604/110
4,838,863 A * 6/1989 Allard ................ A61M 5/3232
604/110
(Continued)

FOREIGN PATENT DOCUMENTS

EP    0 347 742 A1    6/1989
EP    0 787 501 A2    1/1997
(Continued)

*Primary Examiner* — Bhisma Mehta
*Assistant Examiner* — Jenna Zhang
(74) *Attorney, Agent, or Firm* — Saliwanchik, Lloyd & Eisenschenk

(57) ABSTRACT

The present invention relates to a safety syringe (100) having a hollow barrel (1), plunger (2) and a detachable needle support (4), characterized in that the safety syringe (100) includes; a) a piston gasket (3) interference fit with the plunger head (7) of the plunger (2); b) a plurality of bone structures (6) provided at the barrel head (1*a*) of the hollow barrel (1) to temporarily engage and support the needle support (4); c) a plurality of slots (8) longitudinally disposed at one substantial distal end of the needle support (4); and d) stoppers (5) provided at the barrel head (1*a*); wherein a fluid is injected by a first stroke of the plunger (2) under normal load; and an additional load is applied to the plunger (2) to compress the piston gasket (3) so that the plunger head (7) of the plunger (2) travels further to break the bone structures (6) for subsequent retraction of the needle support (4) on a second stroke.

6 Claims, 5 Drawing Sheets

(58) Field of Classification Search
USPC .......................................................... 604/110
See application file for complete search history.

(56) References Cited

U.S. PATENT DOCUMENTS

| | | | | |
|---|---|---|---|---|
| 4,838,869 A | | 6/1989 | Allard | |
| 4,950,253 A | * | 8/1990 | Jacobs | A61M 5/24 |
| | | | | 604/218 |
| 5,000,735 A | * | 3/1991 | Whelan | A61M 5/50 |
| | | | | 604/110 |
| 5,104,378 A | * | 4/1992 | Haber | A61M 5/322 |
| | | | | 604/110 |
| 5,246,423 A | * | 9/1993 | Farkas | A61M 5/31511 |
| | | | | 128/919 |
| 5,725,501 A | * | 3/1998 | Lichtenberg | A61M 5/3205 |
| | | | | 604/110 |
| 5,899,887 A | * | 5/1999 | Liu | A61M 5/322 |
| | | | | 604/110 |
| 2004/0064108 A1 | * | 4/2004 | Krantz | A61M 5/344 |
| | | | | 604/240 |

FOREIGN PATENT DOCUMENTS

| | | |
|---|---|---|
| WO | WO 91/08011 | 6/1991 |
| WO | WO 95/11713 | 5/1995 |

\* cited by examiner

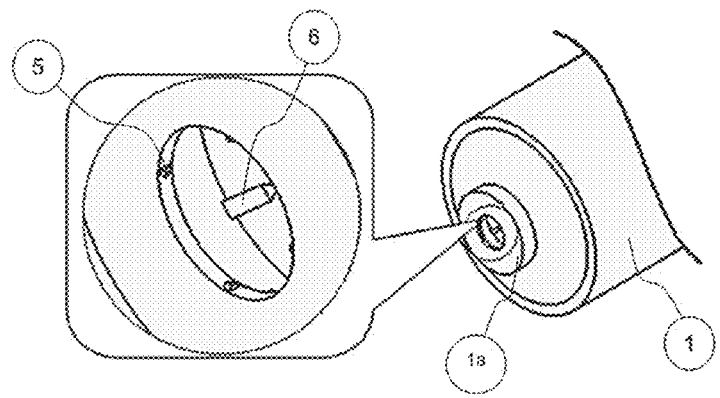
FIG. 3
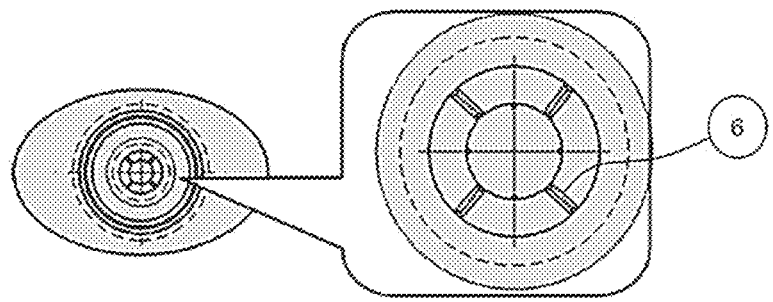
FIG. 4
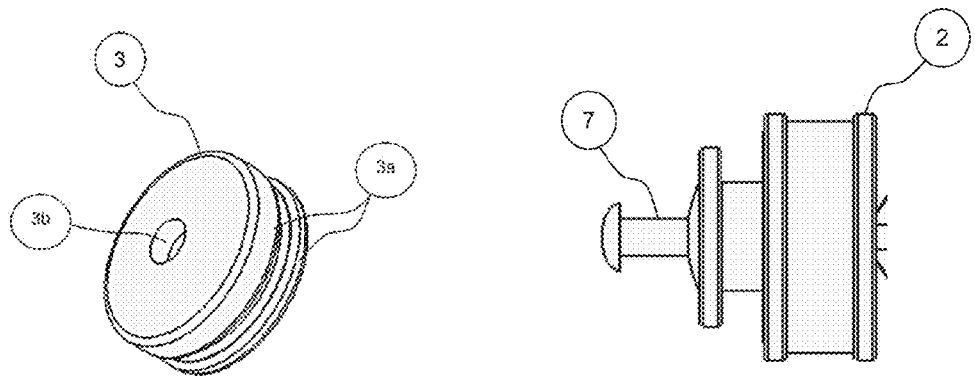
FIG. 5
FIG. 6

SAFETY SYRINGE

CROSS REFERENCE TO A RELATED APPLICATION

This application is a National Stage Application of International Application Number PCT/MY2012/000202, filed Jul. 11, 2012; which claims priority to Malaysia Patent Application No. PI2011700110, filed Jul. 14, 2011; which are incorporated herein by reference in their entirety.

FIELD OF INVENTION

The present invention relates to a syringe and more particularly to a safety syringe with a detachable and disposable needle support for single use.

BACKGROUND OF INVENTION

Syringe is an instrument for injecting or installing fluid such as medicine, vitamin, vaccine and etc. into the body or withdrawing liquid from the body. It is widely use in the medical field not only for injecting medicine it is also used for orally administering liquid medicine to children or animal without using a needle. It is because the accuracy of measuring the dose and easier to squirt the medicine into the mouth instead of using spoon.

In the usage of medical syringes, the reusable of syringes which may lead to cross-infection of diseases is a major factor to be concerned. Therefore, a great need of single use safety syringe to avoid cross-contamination or infection arises due to this concern. The single use safety syringe is useful in wide range of drug therapies for those frequently require a number of daily injections. The safety syringe also becomes great interest for those people who have limited physical ability. As such, the safety syringe should not inject with any diseases through the syringe, including HIV, hepatitis B and C viruses and other pathogens intentionally or accidentally.

Various single use safety syringes which administer subcutaneous medications have been used as being one way to avoid any potential problems. Among many advantages of such single use safety syringes include reduction of environmental pollution associated with contaminated needle disposal. Although many single use safety syringes have achieved public acceptance and commercial success in the marketplace, however, some single use syringes present a variety of problems. Accordingly, it is found that some syringes which claim to be "single use" in actuality can be reused with user intervention. Some syringes are designated as "single use" solely because they are to be discarded after use pursuant to a regulation; nothing prevents their reuse. Some syringe designs expose the drug or bodily fluid contained therein to reactive components of the syringe, e.g. a spring used to retract the plunger. Moreover, some syringes, although not capable of being reused, present health risks to the medical personnel handling them. In addition, there are some factors which may need to be considered such as their sophisticated design, and high cost of contemporary components.

In some countries, plastic disposable syringe is widely used in hospitals. This type of syringe is low cost, easy to handle and can be thrown away after use. However, the problem occurs when most hospital in some countries does not practice the single use safety syringe, but using the normal syringe. The safety syringe such as "auto disable" or "auto retractable" types are usually imported and expensive to use, and not all the hospitals in some countries are unaffordable to use such safety syringe. It is to be found that most of the existing inventions are focusing on manually retractable needle, protective cap and plunger as a safety feature. However, most of the existing inventions are design to retract the needle into the barrel. The design of the existing inventions is good for safety reason, but not convenient for disposal process due to the difficult of separating the metal (needle) and plastic parts (plunger and barrel).

In view of these and other shortcomings of the prior art there is a need in the art for an improved safety syringe. Accordingly, it is an object of the present invention to provide an improved safety syringe with a detachable and disposable needle support for single use.

SUMMARY OF THE INVENTION

The present invention relates to a safety syringe with a detachable and disposable needle support for single use. Accordingly, the safety syringe includes: (a) a piston gasket interference fit with the plunger head of the plunger; (b) a plurality of bone structures provided at the barrel head (1a) of the hollow barrel to temporarily engage and support the needle support; (c) a plurality of slots longitudinally disposed at one substantial distal end of the needle support; and (d) stoppers provided at the barrel head; wherein a fluid is injected by a first stroke of the plunger under normal load; and an additional load is applied to the plunger to compress the piston gasket so that the plunger head of the plunger travels further to break the bone structures for subsequent retraction of the needle support on a second stroke.

Accordingly, the piston gasket has a body with circumference resilient ribs provided thereon and an aperture centrally sited through its body. The aperture holds the piston gasket in place by interference fit with the plunger head. The piston gasket is preferably made from a suitable synthetic rubber or other rubber compound.

In the preferred embodiments, the slots of the needle support are slidably engaged with stoppers provided at the barrel head of the hollow barrel. The stoppers (5) are provided to ensure the needle support (4) is securely mounted to the barrel head (1a) and to block the needle support (4) from being further inserted into the hollow barrel (1).

The present invention consists of several novel features and a combination of parts hereinafter fully described and illustrated in the accompanying description and drawings, it being understood that various changes in the details may be made without departing from the scope of the invention or sacrificing any of the advantages of the present invention.

BRIEF DESCRIPTION OF THE DRAWINGS

The present invention will be fully understood from the detailed description given herein below and the accompanying drawings which are given by way of illustration only, and thus are not limitative of the present invention, wherein:

FIG. 3 is a partially perspective front view of a barrel head with number of stoppers disposed therein according to the embodiments of the present invention;

FIG. 4 is a front view of the barrel head illustrating number of bone structures deposed therein;

FIG. 5 is an enlarged perspective view of a piston gasket in accordance with the preferred embodiments of the present invention;

FIG. 6 is a side view of a plunger head according to the embodiments of the present invention;

DETAILED DESCRIPTION OF THE PREFERRED EMBODIMENTS

The present invention relates to an improved safety syringe with a detachable needle support. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

In accordance with preferred embodiments of present invention, an improved safety syringe with a detachable and disposable needle support for single use is provided. The main objective of this development is to provide a safety syringe with distinctive design to increase the safety characteristic. Where the specific objective is to provide a non-complex design of safety syringe with additional safety features which is simple to operate, similarly with the conventional syringe that requires no specific and additional training for the use of the safety syringe. The disposal criterion of the safety syringe also concentrated to ensure that the design of the safety syringe is easier for disposal.

Accordingly, the improve safety syringe is capable to facilitate the administration of variety of subcutaneous medication. The safety syringe also provides a need for a single use characteristics which includes features such as easy to use, incapable of being reused, avoids cross-contamination or infection and presents no danger to medical personnel after use, and capable of being manufactured at low cost. The improved safety syringe of the present invention also well suited for both self-administrative of medication and for injection of others.

Figure 1:
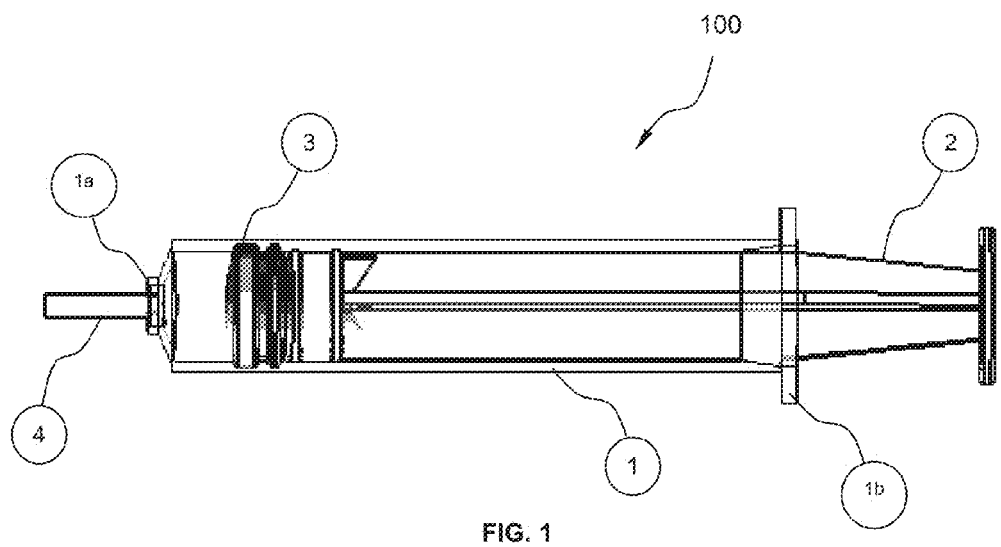
FIG. 1 is an assembled perspective view of a safety syringe in accordance with the preferred embodiments of the present invention.
Figure 2:
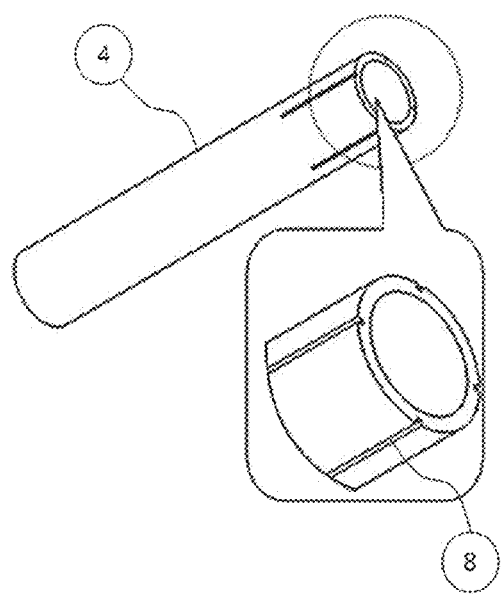
FIG. 2 is a perspective view of a needle support with number of slots provided thereof according to preferred embodiments of the present invention.
Figure 7:
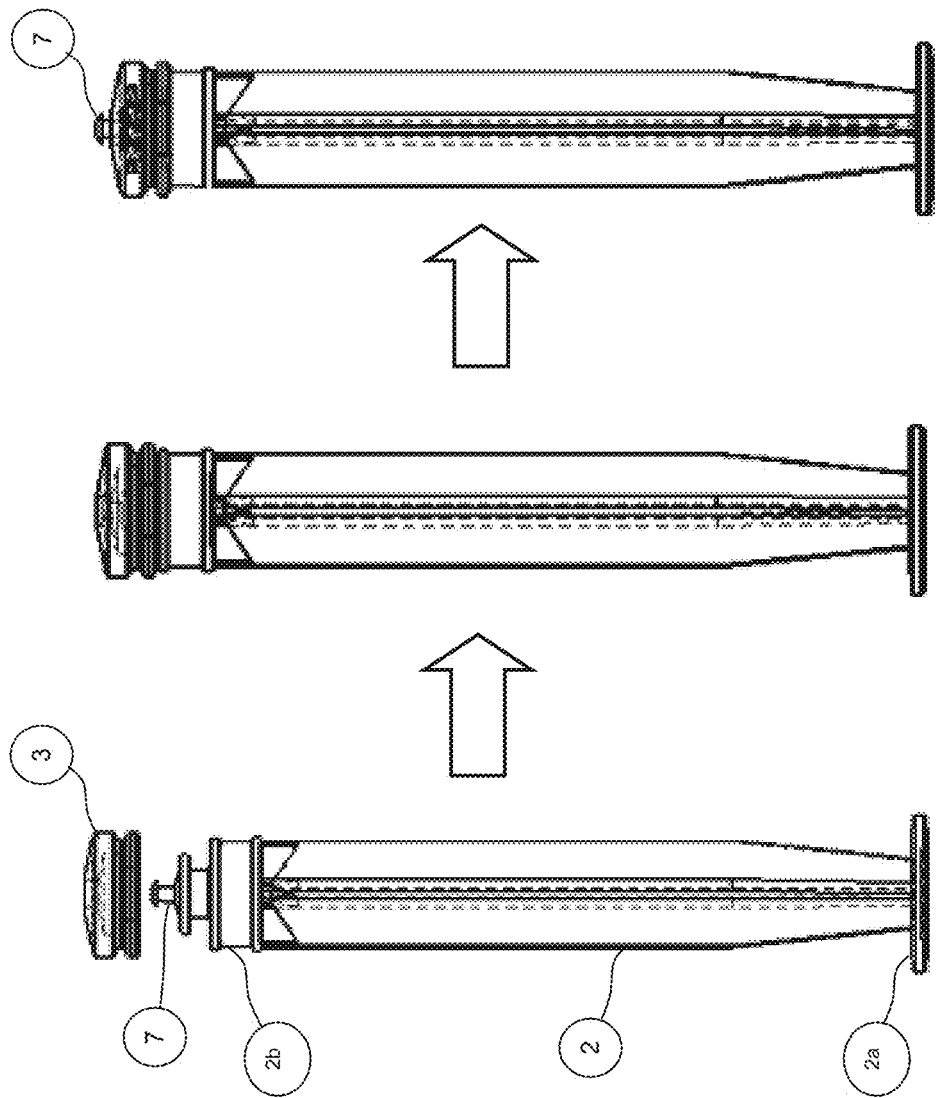
FIG. 7 is a schematic view illustrating assembly sequence of a plunger and the piston gasket.
Figure 8:
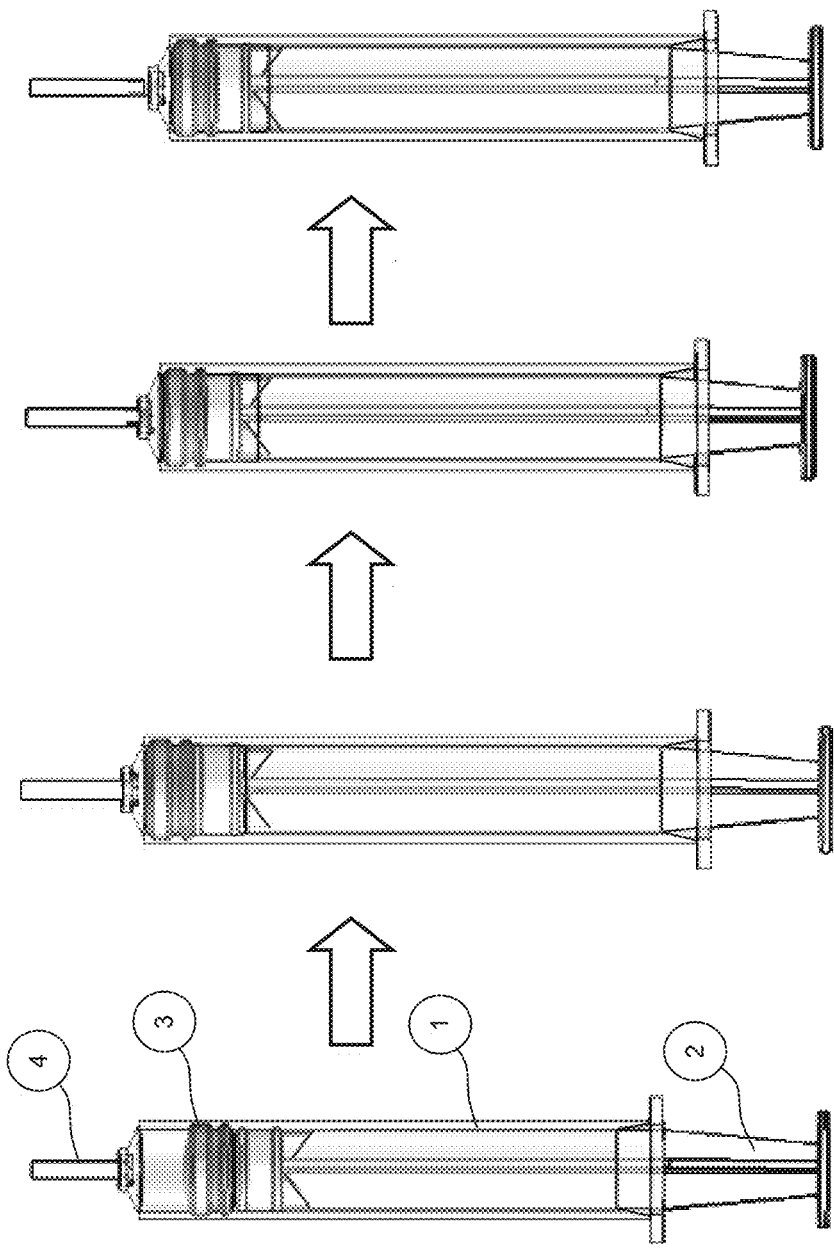
FIGS. 8 and 9 are schematic views of the safety syringe illustrating the detachable sequence of the needle support.
Figure 9:
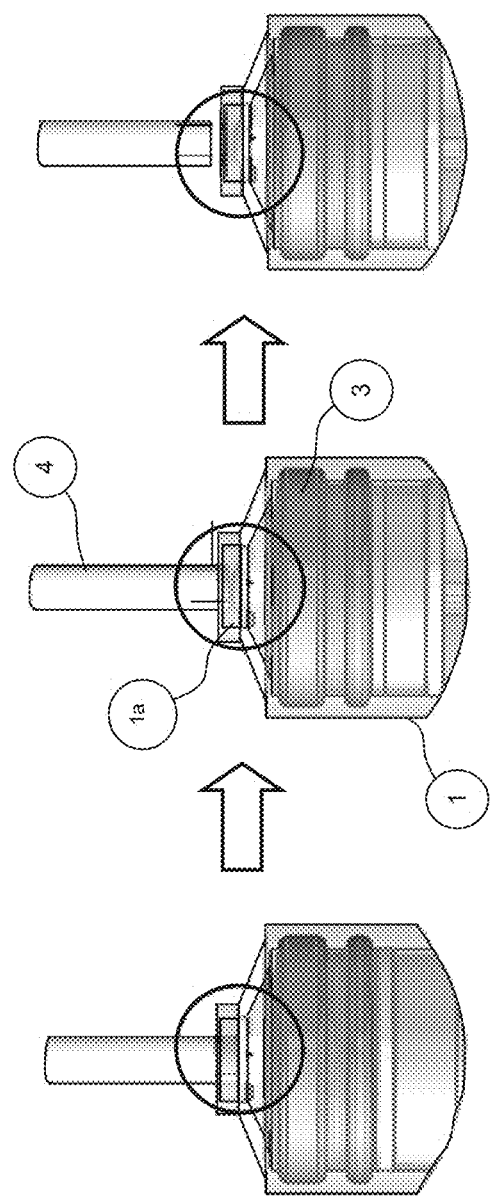

The improved safety syringe according to the preferred embodiments of the present invention will now be described in accordance to the accompanying drawings FIGS. 1 to 9, both individually and in any combination thereof.

The improved safety syringe (100) generally includes a barrel (1), a plunger (2) which is in associated with a piston gasket (3) slidably displaced within the barrel (1), and a detachable needle support (4).

Accordingly, the body of safety syringe (100) is preferably a cylindrical or a standard covering tube for containing and discharging fluid having a hollow barrel (1) and a barrel head (1a) protruded therefrom. The hollow barrel (1) has two opposing open ends and includes annular flange (1b) at one end. Accordingly, the annular flange (1b) extends radially out from one distal open end of the barrel (1) and other open distal end is provided with the barrel head (1a).

In the preferred embodiments, the plunger (2) includes a shaft having a thumb (2a) and a piston end (2b) opposing with each other. It is to be noted that the piston end (2b) is provided with a plunger head (7) extending therefrom. The piston gasket (3) is provided and is attached proximally to the piston end (2b) of the plunger (2). It will be appreciated that the piston end (2b) and the piston gasket (3) maintain a substantially air tight and fluid tight seal in the hollow barrel (1) when the plunger (2) is slidably displaced into and out within the hollow barrel (1). The engagement of the hollow barrel (1) and plunger (2) define a variable vacuum compartment in the hollow barrel (1).

The piston gasket (3) of the preferred embodiments is preferably made from a suitable synthetic rubber or other rubber compound. It will be appreciated the piston gasket (3) has a elastic properties to provide spring energy to the plunger (2) for any additional force applied thereof. Accordingly, the piston gasket (3) includes a body with circumference resilient ribs (3a) provided thereon and an aperture (3a) centrally sited through its body. The aperture (3a) serves to hold the piston gasket (3) in place by interference fit with the plunger head (7). The piston gasket (3) further provides air tight and fluid tight seal of the plunger (2) against inner wall of the hollow barrel (1) of the safety syringe (100) and serves as a collar for the plunger (2). The circumference resilient ribs (3a) of the piston gasket (3) provides compression strength of the piston gasket (3) and to allow the piston gasket (3) to remain at it initial uncompressed length prior to completion of injection. It is to be noted that the piston gasket (3) follows the slidably movement of the plunger (2) within the hollow barrel (1) and can be compressed by additional force or load applied to the plunger over a load which would be considered normal.

The detachable needle support (4) is provided and is temporarily attached to the open distal end of the barrel head (1a). The needle support (4) preferably has plurality of slots (8) longitudinally disposed at one of its substantial distal end. The needle support (4) is detachably mounted to the hollow barrel (1) by plurality of bone structures (6). Accordingly, the slots of the needle support (4) is slidably engaged with stoppers (5) provided at the barrel head (1a) of the hollow barrel (1). The stoppers (5) serve to ensure the needle support (4) is securely mounted to the barrel head (1a) and to block the needle support (4) from being further inserted into the hollow barrel (1). The needle support (4) of the safety syringe (100) can be detached from the barrel head (1a) of the hollow barrel (1) when the additional force is applied towards to the plunger (2).

In the preferred embodiments, the bone structures (6) are provided at the barrel head (1a) to temporarily engage and support the needle support (4). Accordingly, the bone structures (6) are design based on spider web concept to securely hold the needle support (4). It is to be noted that the bone structures (6) will only break if there is additional force acting towards the plunger (2).

In operation, the first downward stroke of the plunger (2) will allowed the fluid to be injected out from the hollow barrel (1). The needle support (4) will not be detached from the barrel head (la) of the hollow barrel (1) if the plunger (1) is pushed in a normal force for medication injection. The needle support (4) will only be detached if the additional force is given towards the plunger (2) that will compressed the piston gasket (3) disposed at the plunger head (7) of the plunger (2). Therefore, when the piston gasket (3) is compressed, the plunger head (7) will move forward and will pushed the needle support (4) to detach from the hollow barrel (1). Accordingly, the needle support (4) can be retracted from the safety syringe (100) and ensured the safety syringe (100) can only be used once.

In more particular, the piston gasket (3) will be compressed under additional load at the completion of injection, so that in a first downward stroke of the plunger (2) under normal load i.e. without additional load applied, the plunger (2) does not engage the needle support (4) so that fluid is injected by the first stroke, but in a second stroke of the plunger (2) after the injection has been completed, additional load is applied to the plunger (2) to compress the piston gasket (3) so that the plunger head (7) of the plunger (2) travels further to break the bone structures (6) for subsequent retraction of the needle support (4) on a second stroke.

The invention being thus described, it will be obvious that the same may be varied in many ways. Such variations are not to be regarded as a departure from the principle and scope of the invention, and all such modifications as would obvious to one skilled in the art intended to be included within the scope of following claims.

The invention claimed is:

1. A safety syringe comprising a hollow barrel having a barrel head; a plunger having a plunger head; and a detachable needle support; characterized in that the safety syringe comprises:
    (a) a piston gasket placed in an interference fit with the plunger head of the plunger;
    (b) a plurality of bone structures within the barrel head, wherein the plurality of bone structures are attached between the barrel head of the hollow barrel and the detachable needle support inserted within the barrel head, such that the plurality of bone structures support and temporarily connect the detachable needle support to the barrel head;
    (c) a plurality of slots longitudinally disposed at one substantially distal end of the detachable needle support; and
    (d) stoppers on the barrel head engage with the plurality of slots and inhibit capable of inhibiting the detachable needle support from being advanced into the hollow barrel;

such that, when a fluid is injected by a first stroke of the plunger under normal load and an additional load is applied to the plunger one a second stroke to compress the piston gasket, the plunger head of the plunger advances out from the piston gasket to contact and break the plurality of bone structures thereby permanently disengaging the detachable needle support from the barrel head and making the detachable needle support incapable of reuse.

2. The safety syringe according to claim 1, wherein the piston gasket has a body with circumference resilient ribs provided thereon and an aperture centrally sited through the body.

3. The safety syringe according to claim 2, wherein the aperture holds the piston gasket in place by interference fit with the plunger head.

4. The safety syringe according to claim 1, wherein the piston gasket is made from a synthetic rubber or other rubber compound.

5. The safety syringe according to claim 1, wherein the plurality of slots on the detachable needle support are slidably engaged with the stoppers provided on the barrel head of the hollow barrel.

6. The safety syringe according to claim 1, wherein the stoppers are provided to further support and ensure the detachable needle support is securely mounted to the barrel head and to block the detachable needle support from being further inserted into the hollow barrel.

* * * * *